(12) United States Patent
Sliwa et al.

(10) Patent No.: US 11,051,877 B2
(45) Date of Patent: Jul. 6, 2021

(54) MEDICAL DEVICE WITH CONTACT FORCE SENSING TIP

(71) Applicant: St. Jude Medical, Cardiology Division, Inc., St. Paul, MN (US)

(72) Inventors: John W. Sliwa, San Jose, CA (US); Alon Izmirli, Ganot Hadar (IL); Zhenyi Ma, Santa Clara, CA (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 979 days.

(21) Appl. No.: 15/030,064

(22) PCT Filed: Nov. 6, 2014

(86) PCT No.: PCT/US2014/064335
§ 371 (c)(1),
(2) Date: Apr. 17, 2016

(87) PCT Pub. No.: WO2015/069887
PCT Pub. Date: May 14, 2015

(65) Prior Publication Data
US 2016/0228180 A1      Aug. 11, 2016

Related U.S. Application Data

(60) Provisional application No. 61/962,466, filed on Nov. 7, 2013.

(51) Int. Cl.
*A61B 18/14*     (2006.01)
*A61B 5/00*      (2006.01)
(Continued)

(52) U.S. Cl.
CPC .......... *A61B 18/1492* (2013.01); *A61B 5/283* (2021.01); *A61B 5/6885* (2013.01);
(Continued)

(58) Field of Classification Search
None
See application file for complete search history.

(56) References Cited

U.S. PATENT DOCUMENTS

| | | | |
|---|---|---|---|
| 5,425,367 A * | 6/1995 | Shapiro | A61B 5/06 128/899 |
| 7,263,397 B2 | 8/2007 | Hauck et al. | |

(Continued)

FOREIGN PATENT DOCUMENTS

| | | |
|---|---|---|
| EP | 2338428 | 6/2011 |
| EP | 2641555 | 9/2013 |

(Continued)

OTHER PUBLICATIONS

International Search Report for PCT Application No. PCT/US2014/064335, dated Feb. 6, 2015. 5 pgs.

*Primary Examiner* — Oommen Jacob
*Assistant Examiner* — Shahdeep Mohammed
(74) *Attorney, Agent, or Firm* — Dykema Gossett PLLC

(57) ABSTRACT

Medical devices for diagnosis or treatment of tissue in a body. Representative devices include an elongate shaft having a proximal portion and a distal portion configured for movement relative to the proximal portion. A flexible member having a predetermined stiffness is disposed between the proximal and distal portions. One or more coils and an electrically passive element are disposed within the shaft with either the coils or element configured for movement with the distal portion. The element comprises a material effecting an electrical characteristic of the coils. Movement of the distal portion in response to its contact with the tissue and relative movement of the coils and element causes a change in the electrical characteristic in at least one of the coils indicative of at least a contact force magnitude between the distal portion and the tissue. Several embodiments allow (Continued)

determination of both force magnitude and force vector direction.

20 Claims, 7 Drawing Sheets

(51) Int. Cl.
 *A61B 5/283* (2021.01)
 *A61B 8/12* (2006.01)
 *A61B 90/00* (2016.01)
 *A61B 18/12* (2006.01)
 *A61B 5/287* (2021.01)

(52) U.S. Cl.
 CPC ............ *A61B 8/12* (2013.01); *A61B 18/1206* (2013.01); *A61B 5/287* (2021.01); *A61B 2090/064* (2016.02); *A61B 2090/065* (2016.02); *A61B 2562/0223* (2013.01); *A61B 2562/0261* (2013.01)

(56) References Cited

U.S. PATENT DOCUMENTS

| | | | |
|---|---|---|---|
| 7,386,339 | B2 | 6/2008 | Strommer et al. |
| 7,914,515 | B2 | 3/2011 | Heideman et al. |
| 8,357,152 | B2 | 1/2013 | Govari et al. |
| 2001/0034501 | A1* | 10/2001 | Tom .................. A61B 17/3207 604/67 |
| 2008/0091193 | A1* | 4/2008 | Kauphusman ..... A61B 18/1492 606/41 |
| 2009/0138007 | A1* | 5/2009 | Govari ................ A61B 1/0008 606/33 |
| 2009/0247942 | A1 | 10/2009 | Kirschenman |
| 2009/0247944 | A1 | 10/2009 | Kirschenman et al. |
| 2009/0247993 | A1 | 10/2009 | Kirschenman et al. |
| 2009/0248042 | A1 | 10/2009 | Kirschenman |
| 2009/0299174 | A1* | 12/2009 | Wright .................... A61B 5/06 600/424 |
| 2009/0306650 | A1* | 12/2009 | Govari ............... A61B 18/1492 606/41 |
| 2010/0249576 | A1* | 9/2010 | Askarinya ................ A61B 5/06 600/424 |
| 2010/0256558 | A1 | 10/2010 | Olson et al. |
| 2011/0015569 | A1 | 1/2011 | Kirschenman et al. |
| 2011/0152721 | A1 | 6/2011 | Sela et al. |
| 2011/0184406 | A1 | 7/2011 | Selkee |
| 2014/0039258 | A1* | 2/2014 | Sekiguchi ............... A61B 5/062 600/117 |

FOREIGN PATENT DOCUMENTS

| | | |
|---|---|---|
| JP | 2001-141409 A | 5/2001 |
| JP | 2001-159505 A | 6/2001 |
| JP | 2010-131390 A | 6/2010 |
| JP | 2011-147783 A | 8/2011 |
| WO | 2001/70117 A2 | 9/2001 |
| WO | 2002/021995 | 3/2002 |
| WO | 2009/120982 A2 | 10/2009 |
| WO | 2013019544 | 2/2013 |

* cited by examiner

MEDICAL DEVICE WITH CONTACT FORCE SENSING TIP

BACKGROUND a. Field

This disclosure relates to a medical device for diagnosis or treatment of tissue in a body. In particular, the instant disclosure relates to a device that provides an indication of contact force between the device and the tissue.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks.

Some catheters include components for determining contact between the catheter and tissue and for controlling the catheter in response to the contact. In the case of an electrophysiological diagnostic or mapping catheter, for example, contact is desirable to provide meaningful sensor outputs and accurate mapping of the heart. In the case of ablation catheters, sufficient contact is desirable for effective formation of ablative lesions in the tissue.

The foregoing discussion is intended only to illustrate the present field and should not be taken as a disavowal of claim scope.

SUMMARY

Among other things, various embodiments disclosed herein are directed to medical devices, systems and methods for diagnosis or treatment of tissue in a body. For example, the instant disclosure describes devices and systems that provide an indication of contact force between a device and the tissue using an electrically passive element in a distal portion of the device whose movement effects an electrical characteristic in one or more coils housed in a proximal portion of the device with the proximal portion of the device separated from the distal portion of the device by a flexible member such as a spring.

A medical device for the diagnosis or treatment of tissue in a body in accordance with one embodiment of the present teachings includes an elongate, tubular shaft configured to be received within the body. The shaft has a proximal portion and a distal portion configured for movement relative to a distal end of the proximal portion including by movement towards and away from the distal end of the proximal portion along a longitudinal axis of the shaft and by deflection from the longitudinal axis. The device further includes a flexible member disposed between the proximal and distal portions of the shaft. The flexible member has a predetermined stiffness. The device further includes an electromagnetic coil disposed within the shaft and an electrically passive element disposed within the shaft. The electrically passive element comprises a material effecting an electrical characteristic of the electromagnetic coil and may comprise a ferrite or unpoled magnetic material in certain embodiments. One of the electromagnetic coil and the electrically passive element is configured for movement with the distal portion of the shaft and relative to the other of the electromagnetic coil and the electrically passive element. Relative movement between the electromagnetic coil and the electrically passive element in response to contact of the distal portion with the tissue and deformation of the flexible member causes a change in the electrical characteristic in the electromagnetic coil. The change is indicative of the deformation of the flexible member and a specific contact force between the distal portion and the tissue.

A system for the treatment or diagnosis of tissue within a body includes a medical device having an elongate, tubular shaft configured to be received within the body. The shaft has a proximal portion and a distal portion configured for movement relative to a distal end of the proximal portion including by movement towards and away from the distal end of the proximal portion along a longitudinal axis of the shaft and by deflection from the longitudinal axis. The device further includes a flexible member disposed between the proximal and distal portions of the shaft. The flexible member has a predetermined stiffness. The device further includes an electromagnetic coil disposed within the shaft and an electrically passive element disposed within the shaft. The electrically passive element comprises a material effecting an electrical characteristic in the electromagnetic coil and may comprise a ferrite or unpoled magnetic material in certain embodiments. One of the electromagnetic coil and the electrically passive element is configured for movement with the distal portion of the shaft and relative to the other of the electromagnetic coil and the electrically passive element. Relative movement between the electromagnetic coil and the electrically passive element in response to contact of the distal portion with the tissue and deformation of the flexible member causes a change in the electrical characteristic in the electromagnetic coil. The change is indicative of the deformation of the flexible member and a specific contact force between the distal portion and the tissue. The system further includes an electronic control unit configured to determine the specific contact force magnitude responsive to a signal generated by the electromagnetic coil indicative of the change in the electrical characteristic of the electromagnetic coil.

A medical device and system in accordance with the present teachings is advantageous relative to conventional devices and systems. A medical device and system in accordance with the present teachings provide means for measuring contact force magnitude between the device and tissue in the body that can be less complex and less expensive than conventional devices and systems which also report the absolute vector orientation of the net force in three dimensional space. The use of an electrically passive element in the device reduces the number of conductors needed within the device for determining contact force as compared to conventional devices. As a result, the device and system conserve valuable space within the device and are less expensive to manufacture.

The foregoing and other aspects, features, details, utilities, and advantages of the present teachings will be apparent from reading the following description and claims, and from reviewing the accompanying drawings.

DETAILED DESCRIPTION OF EMBODIMENTS

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a physician manipulating one end of an instrument used to treat a patient. The term "proximal" refers to the portion of the instrument closest to the physician and the term "distal" refers to the portion located furthest from the physician. Similarly, "more proximal" means closer to the physician whereas "more distal" means further form the physician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
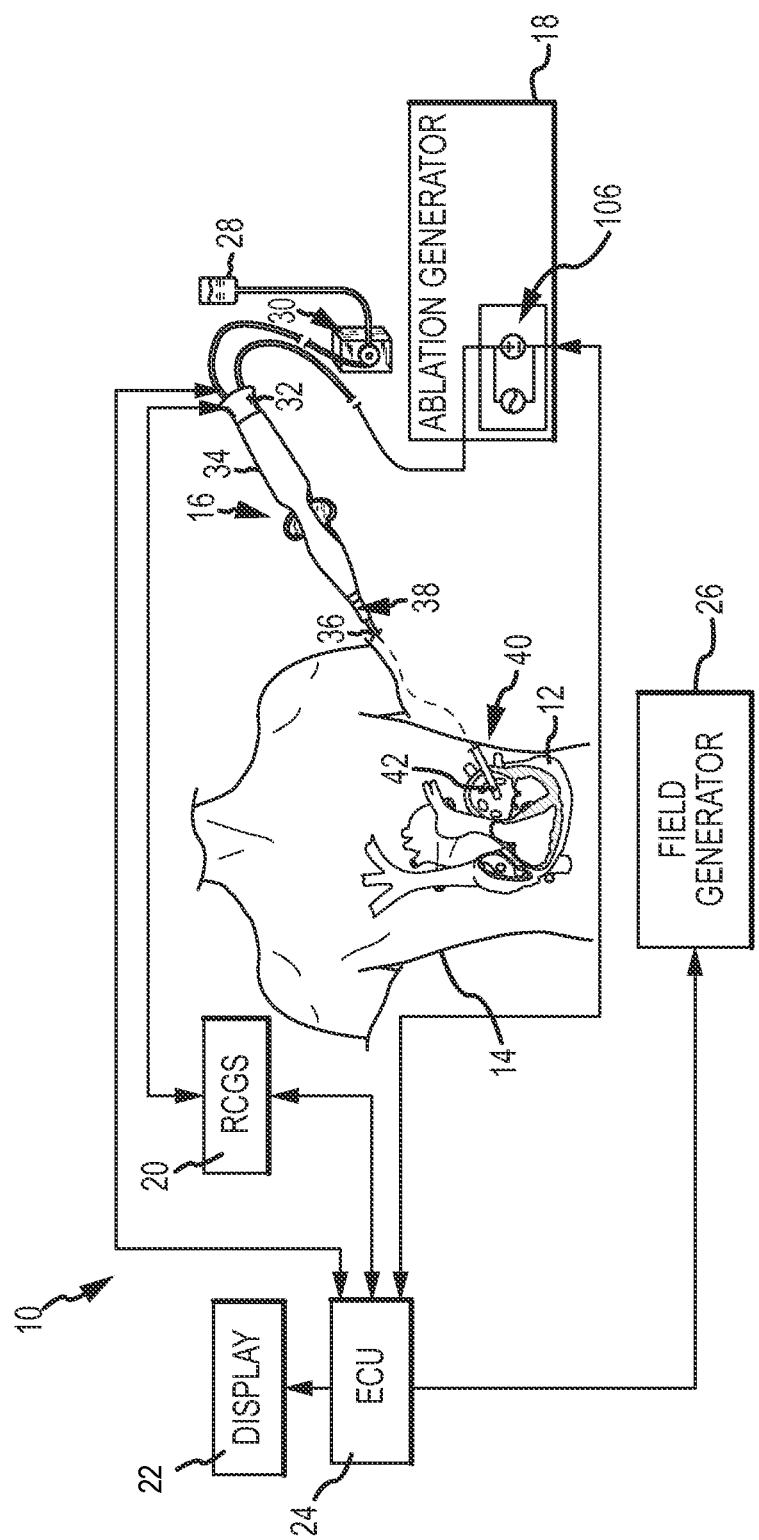
FIG. 1 is diagrammatic view of one embodiment of a system for diagnosis or treatment of tissue in a body in accordance with one embodiment of the present teachings.
Figure 2:
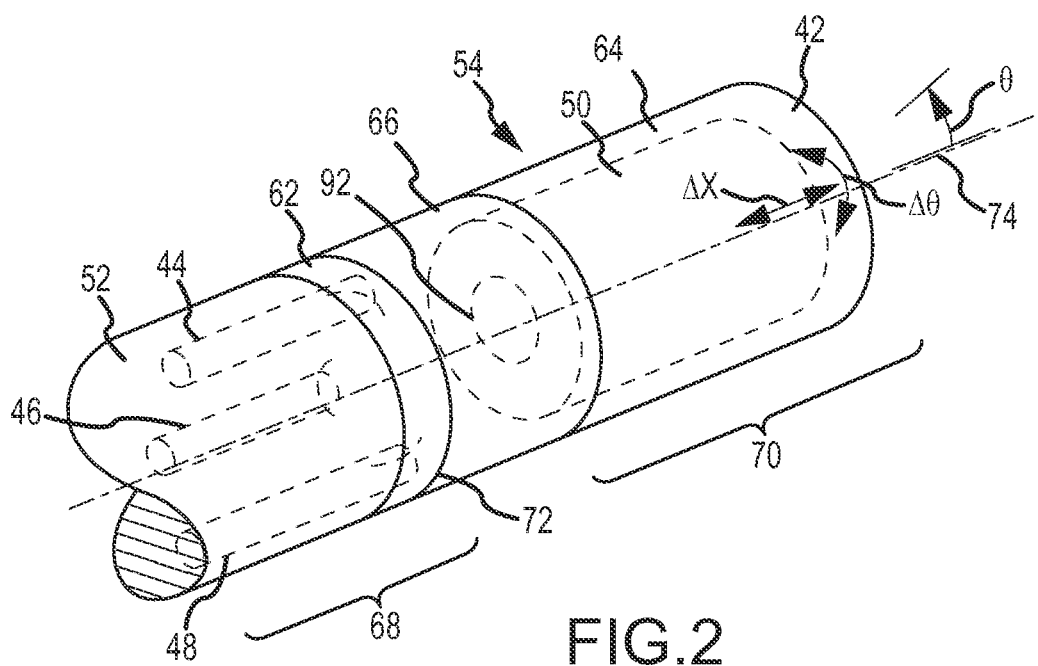
FIG. 2 is an isometric view of a portion of a medical device for diagnosis or treatment of tissue in accordance with one embodiment of the present teachings.
Figure 3:
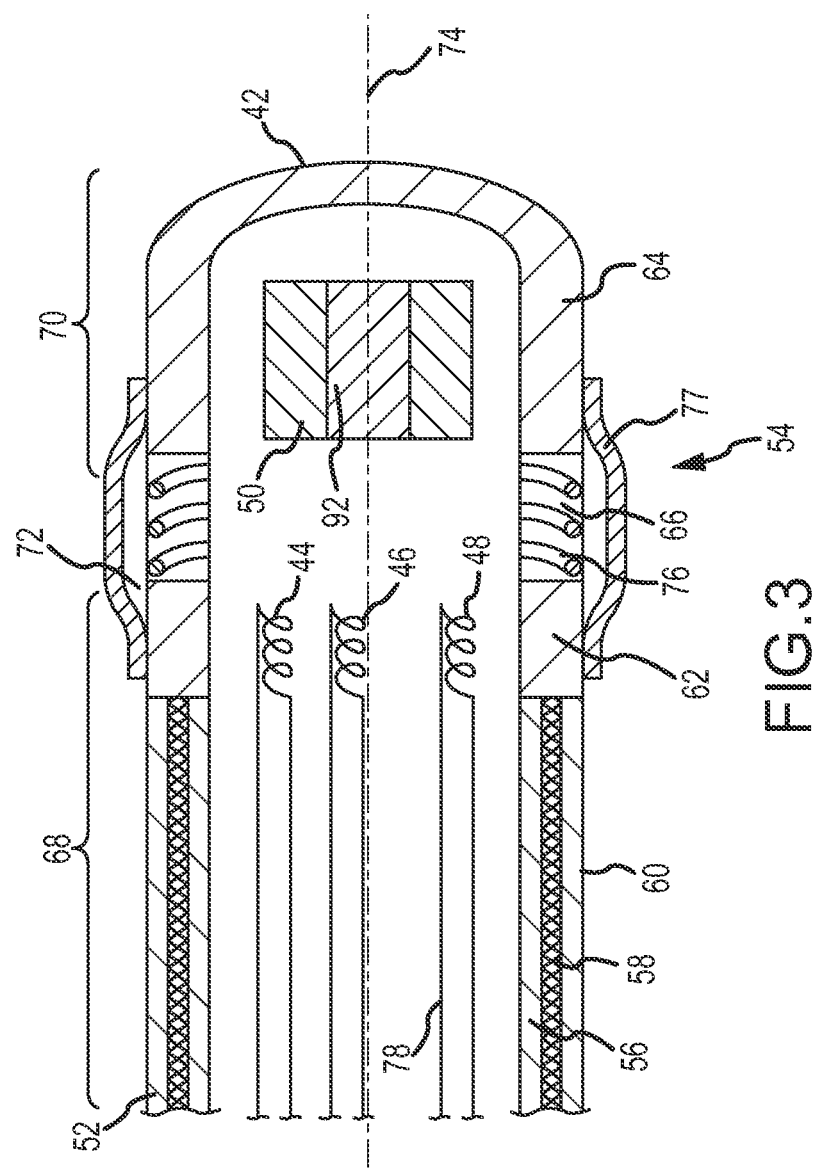
FIG. 3 is a sectional view of the medical device of FIG. 2.

Referring now to the drawings wherein like reference numerals are used to identify identical or similar components in the various views, FIG. 1 illustrates one embodiment of a system 10 for diagnosis or treatment of tissue 12 in a body 14. In the illustrated embodiment, tissue 12 comprises cardiac tissue within a human body. It should be understood, however, that a system 10 in accordance with the present teachings may find application in connection with procedures for the diagnosis or treatment of a variety of tissues in human and non-human bodies. System 10 includes a medical device for diagnosis or treatment of tissue 12. In accordance with one embodiment, system 10 includes an ablation catheter 16 for diagnosis or treatment of tissue 12 and may further include an ablation generator 18, a remote catheter guidance system (RCGS) 20, a display system 22, an electronic control unit (ECU) 24, and/or an external field generator 26. Catheter 16 is provided for examination, diagnosis and treatment of internal body tissues such as tissue 12. In accordance with one embodiment of the present teachings, catheter 16 comprises an ablation catheter and, more particularly, an irrigated radio-frequency (RF) ablation catheter. It should be understood, however, that catheter 16 is provided for illustration only and that system 10 could be adapted for use with other types of catheters including electrophysiology (EP) mapping catheters and intracardiac echocardiograph (ICE) catheters, as well as for use with other types of ablation catheters including those providing different types of ablation energy (e.g., cryoablation, ultrasound, laser, microwave, electroporation, etc.) and/or those sized and configured to access different areas of patient's body or cardiovascular system, such as, for example, the renal arteries. Further, it should be understood that system 10 can be adapted for use with other types of medical devices used in the diagnosis or treatment of tissue 12 including, for example, introducer sheaths or catheters used to install artificial heart valves, tiny pacemakers or other implants. Catheter 16 may be connected to an irrigant fluid source 28 having a biocompatible fluid such as saline which is passed through an irrigation pump 30 (which may comprise, for example, a fixed rate roller pump or variable volume syringe pump with a gravity feed supply from fluid source 28 as shown) for irrigation. Catheter 16 may also be electrically connected to ablation generator 18 for delivery of ablating RF energy. Catheter 16 may include a cable connector or interface 32, a handle 34, a flexible shaft 36 having a proximal end 38 and a distal end 40 and one or more ablation and sensing electrodes 42. Catheter 16 may also include other conventional components not illustrated herein such as a temperature sensor, additional pacing or mapping electrodes, and corresponding conductors or leads. Referring to FIGS. 1-3, in accordance with the present teachings, catheter 16 may further include means, such as electromagnetic coils 44, 46, 48, and element 50, for sensing a contact force of the distal end 40 of catheter 16 with tissue 12.

Referring again to FIG. 1, connector 32 provides mechanical, fluid and electrical connection(s) for cables extending from ablation generator 18, RCGS 20, and pump 30. Connector 32 is conventional in the art and is disposed at a proximal end of catheter 16. Although directly attached to handle 34 in the illustrated embodiment, connector 32 may be coupled to handle 34 indirectly through, for example, several feet of cable. Handle 34 provides a location for the physician to hold catheter 16 and may further provides means for steering or guiding shaft 36 within body 14. For example, handle 34 may include means to change the length of a steering wire extending through catheter 16 to distal end 40 of shaft 36 to control translation and/or deflection of the distal end 40 of shaft 36 to steer shaft 36.

Handle 34 may be manipulated manually by a physician or automatically through, for example, robotic controls such as RCGS 20. It should be understood that the construction of handle 34 may vary and may be absent in a fully-robotic implementation of the system.

With reference to FIGS. 1 and 2 again shaft or flexible lumen 36 provides structural support to other components of catheter 16 including electrodes 42, coils 44, 46, 48, and element 50, wires and other conductors extending to electrodes 42 and coils 44, 46, 48 and possibly additional electronics used for signal processing or conditioning. Shaft 36 may also permit transport, delivery, and/or removal of fluids (including irrigation fluids and bodily fluids), medicines, and/or surgical tools or instruments. Shaft 36 may also support a tissue imaging device in the distal tip. Shaft 36 is configured to be received within body 14 and may be introduced into a blood vessel or other structure within body 14 through a conventional introducer. Shaft 36 may then be steered or guided through body 14 to a desired location such as tissue 12 with a guiding introducer such as the Agilis™ N×T steerable introducer available from St. Jude Medical, Inc., with RCGS 20, or with guide wires, pullwires or other means known in the art. Referring to FIGS. 2-3, shaft 36 may include an elongate, tubular member 52 and a tip assembly 54.

Member 52 is flexible or deformable and configured for movement within body 14 (FIG. 1). Member 52 also defines one or more lumens configured to house conductors and steering wires and to allow fluids to pass therethrough. Referring to FIG. 3, member 52 may include a tubular, polymeric inner liner 56, a braided wire layer 58 for torque transfer, and an outer polymeric jacket 60. Liner 56 may be made from a polymeric material such as polyfluoroethylene (PTFE) including PTFE sold under the registered trademark "TEFLON" by E.I. DuPont de Nemours & Co. Corp, polyether block amides, nylon or thermoplastic elastomers such as the elastomer sold under the registered trademark "PEBAX" by Arkema, Inc. Braided wire layer 58 is configured to provide appropriate levels of pushability, torqueability, flexibility, and kink resistance to shaft 36. Layer 58 may be formed from stainless steel wire, and may be flat wire (wire having a cross-section that, when taken along the wire's longitudinal axis and measured along two orthogonal axes, is substantially rectangular) arranged in various braid patterns including one-over-one (involving at least two wires) or two-over-two (involving at least four wires) crossover patterns. The wire may be coated with a layer of an insulating material. The wire braid may be directly wound about liner 56 or placed on a core that is slid over liner 56. Jacket 60 is made from a polymeric material such as polyfluoroethylene (PTFE) including PTFE sold under the registered trademark "TEFLON" by E.I. DuPont de Nemours & Co. Corp, polyether block amides, nylon or thermoplastic elastomers such as the elastomer sold under the registered trademark "PEBAX" by Arkema, Inc. and may be extruded over layer 58. Additional details regarding several exemplary catheter constructions may be found in commonly assigned U.S. Pat. No. 7,914,515, the entire disclosure of which is incorporated herein by reference. Member 52 may further be configured to receive tip assembly 54 at a distal end of member 52.

Referring still to FIGS. 2-3, tip assembly 54 includes a more proximal tip portion 62, a more distal tip portion 64 and an intermediate tip portion 66 between portions 62, 64. Proximal tip portion 62 is configured for mounting tip assembly 54 to member 52 at a distal end of member 52. Proximal tip portion 62 extends from the distal end of member 52 to intermediate tip portion 66. Proximal tip portion 62 may be made from a material or materials that are relatively rigid and at least more rigid than materials used to form intermediate tip portion 66 which has finite controlled flexibilities or stiffnesses respectively along its axial (longitudinal compression or stretching direction) and its bending (angulation) direction such as found in a spring. Together with member 52, proximal tip portion 62 may form a proximal portion 68 of shaft 36. Distal tip portion 64 may comprise, or may be configured to support, electrode 42. Distal tip portion 64 extends from an opposite side of intermediate tip portion 66 relative to proximal tip portion 62. Distal tip portion 64 may also be made from a material or materials that are relatively rigid and at least more rigid than materials used to form flexible intermediate tip portion 66. Distal tip portion 64 forms a distal portion 70 of shaft 36. Intermediate tip portion 66 provides a means for allowing movement of the distal portion 70 of shaft 36 relative to a distal end 72 of proximal portion 68 of shaft 36 including movement towards and away from distal end 72 of proximal portion 68 along a longitudinal axis 74 of shaft 36 and by angular or bending deflection from axis 74. Intermediate tip portion 66 is made from a material or materials that are inherently relatively flexible or, alternatively, is rendered more flexible as by slotting or slitting or use of a coil-like structure and thereby at least more flexible than materials used to form proximal and distal tip portions 62, 64. Intermediate tip portion 66 defines or includes a flexible member such as a spring 76 or elastomeric bending rod(s) having at least one predetermined or known stiffness (i.e., a measure of deformation such as grams per degree or grams per millimeter during at least one specific deformation state such as bending, compression, etc.) such that deformation of the flexible member in response to force is known and a detected deformation can be translated to a force by using a look-up table or other data structure in a memory or by using an algorithm. Spring 76 may comprise a helical, coiled, wave or bellows spring and may be made from a variety of materials including metals and metal alloys such as stainless steel, platinum, platinum alloy, titanium, beryllium-copper, nickel titanium (Nitinol) and Invar as well as elastomeric polymers. Spring 76 may also be formed using subtractive laser etching or, electrical discharge machining as from a metal cylindrical tube. Intermediate tip portion 66 may include a single spring 76 centered about axis 74 or a plurality of springs disposed about axis 74 (e.g., three springs spaced equally circumferentially about axis 74). In place of spring 76, intermediate tip portion 66 may alternatively be formed from elastomeric materials including, for example, rubber, such that the flexible element is formed as a small disc or torus centered on axis 74.

Tip assembly 54 may further include a sleeve 77 surrounding intermediate tip portion 66 to prevent ingress of blood from body 14 into the interior of tip assembly 54 and/or egress of saline or other fluids from the interior of tip assembly 54 into the body 14. Sleeve 77 may be sealed to exterior surfaces of tip assembly 54 near the distal end of proximal tip portion 62 and the proximal end of distal tip portion 64. Sleeve 77 may be made from a thin flexible tubular elastomeric material. Sleeve 77 may be formed (such as by it being thin and very stretchable) so as not to significantly alter (e.g., increase) the overall effective stiffnesses of tip 54 as determined preferably only by spring 76. Accordingly, sleeve 77 may be selected so that its shape, configuration and material properties have a minimal or no impact on the stiffness of spring 76 or similar flexible member and so that the any stiffness of sleeve 77 does not vary, or has relatively little variation, despite changes in temperature in tip member 54 and prolonged exposure to blood, saline or other fluids in body 14 and catheter 16. Accordingly, sleeve 77 may be configured so that any stiffness of sleeve 77 is less than 10% of the stiffness of spring 76 in one embodiment, and in another embodiment less than 5% of the stiffness of spring 76 and, in another embodiment, less than 2% of the stiffness of spring 76. Sleeve 77 may also be configured by material selection or application of coatings so that it has very low water absorption to prevent swelling of sleeve 77 and changes in size and stiffness due to such swelling. In particular, sleeve 77 may be configured so that its fluid absorption is less than 10% by weight and, in one embodiment, less than 5% by weight and, in another embodiment, less than 2% by weight. Sleeve 77 may also be formed with corrugations (none shown) to reduce stiffness. Sleeve 77 may also be formed as a relatively thin walled deformable membrane (or balloon) that can be selectively urged away from spring 76 through fluid (e.g., saline) inflation.

Referring again to FIG. 1, electrodes 42 on the outer surface of member 52 or tip portion 54 are provided for a variety of diagnostic and therapeutic purposes including, for example, electrophysiological studies, catheter identification and location, pacing, and cardiac mapping and ablation. In the illustrated embodiment, catheter 16 includes an ablation tip electrode 42 at distal end 40 of shaft 36 that functions as a radio-frequency ablation delivery element. Catheter 16 may also include one or more ring electrodes (not shown) proximal of tip electrode 42 that may be used to obtain electrograms for tissue 12 and for other conventional purposes. It should be understood, however, that the number, orientation, and purpose of electrodes 42 may vary. Electrodes 42 may be made from various electrically conductive materials including those containing gold, platinum, iridium, palladium, rhodium, stainless steel, and/or any combination thereof.

Figure 4:
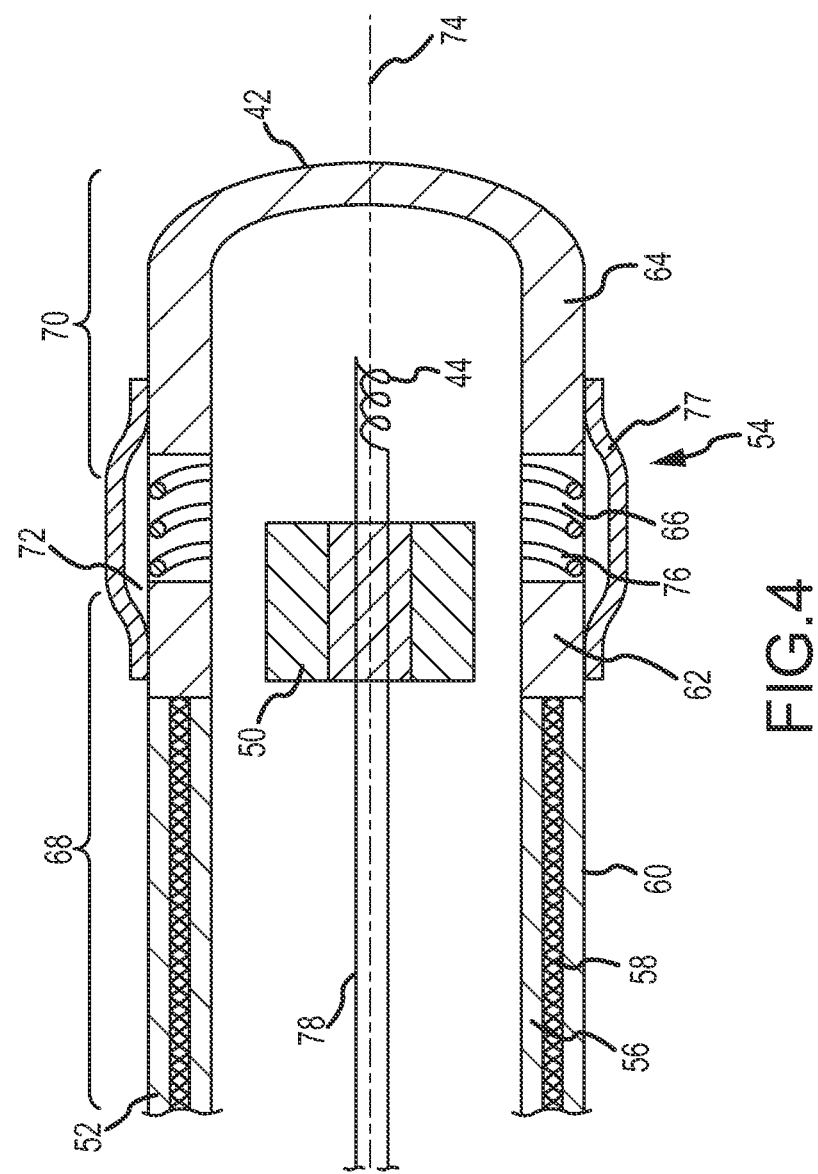
FIG. 4 is a sectional view of a portion of a medical device for diagnosis or treatment of tissue in accordance with another embodiment of the present teachings.

Referring again to FIGS. 2-3, electromagnetic coils 44, 46, 48 and element 50 provide a means for sensing contact force between distal portion 70 of shaft 36 and tissue 12 (see FIG. 1) and therefore together form a force sensor. The illustrated embodiment of FIGS. 2 and 3, having three coils, is capable of reporting both the magnitude of the force subvectors (radial or bending and axial or longitudinal) as well as the absolute three dimensional orientation of those subvectors relative to the more proximal catheter portion 68. Coils 44, 46, 48 generate signals, when electrically excited, which vary predictably in response to the axial and bending position of element 50/tip 54 and that are transmitted to ECU 24. i.e. The electrical coupling of each coil to element 50 varies predictably with their relative orientation/position relative to element 50 and this behavior can be recorded or modeled in system software or in a lookup table. In the embodiment illustrated in FIGS. 2-3, coils 44, 46, 48 are disposed in proximal portion 68 of shaft 36 while element 50 is disposed in the distal deflectable portion 70 of shaft 36. Referring to FIG. 4, however, it should be understood that the positions of coils 44, 46, 48 and element 50 may be reversed such that one or more coils 44, 46, 48 could alternatively be disposed in distal portion 70 while one or more elements 50 is disposed in proximal portion 68. Further, although coils 44, 46, 48 and element 50 are shown in FIGS. 2-3 as disposed entirely within proximal tip portion 62 or distal tip portion 64, it should be understood that coils 44, 46, 48 and/or element 50 may at least partially extend into intermediate tip portion 66 to reduce the axial length of the force sensor.

"Degree of contact" refers to the magnitude of the net vector contact force. The net force magnitude comprises a sensed axial (longitudinal) force vector magnitude component and a sensed angular or bending contact force vector magnitude component normal to the longitudinal axis. These two vector magnitude subcomponents are normal to each other and when vector-summed indicate the combined force magnitude upon the tissue. The net magnitude of the net force vector is directed upon the tissue. While specific embodiments disclosed herein detect the true three dimensional orientation of the two subvectors and net vector it is not a requirement of the systems and apparatus disclosed herein to present to the user the vector orientations even if said vectors are used to compute the reported net force magnitude. Presentation of the orientation is an option permitted by certain embodiments of the invention as described. Physics requires that the net force is resisted or balanced by an equal and opposite force magnitude of the tissue upon the tip. This results in the "degree of contact" needing to detect net force magnitude. The embodiments disclosed herein may or may not also provide to the user true three dimensional orientation of those two force subvectors and net vector. This additional information is useful to "paint" the force subvectors and net vectors on a spatial navigation display in relationship to the catheter tip. However, the orientations aren't required to know the net force magnitude (as opposed to net force spatial orientation) and it can be assumed that the net force magnitude is directed into or toward the contacted tissue.

Again, a system which provides both force subvector magnitudes and their spatial directions relative to the proximal shaft 68 would preferably contain three coils opposite a single ferrite element as in FIGS. 2 and 3. Both the force magnitudes and vector orientations positions can be determined A less accurate but still useful system as disclosed herein can detect a combined vector summed force magnitude only-and with less accuracy than the systems of FIGS. 2 and 3. Specifically, if we look at FIG. 4 we see depicted a single coil opposed to a single ferrite. In the example shown the coil is in the most distal tip however it may be reversed and placed in more proximal catheter section 68. It will be appreciated that the electrical coupling of the single ferrite and single coil of FIG. 4 will also vary with tip 54 deflections. However, with this arrangement the system cannot differentiate between bending and axial deflections.- The system can only detect a combined (bending plus compression) electrical coupling change. Despite this the system can still set a desired minimum force magnitude. As the bending and axial stiffnesses of the spring typically aren't equal and the system doesn't know how much of the detected coupling change is assigned to each then this amounts to a less expensive but less accurate arrangement than that of FIGS. 2 and 3.

Referring again to FIGS. 2-3, coils 44, 46, 48 generate signals indicative of the position of coils 44, 46, 48 relative to element 50 and, therefore, indicative of the position of distal tip portion 70 of catheter 16. In the illustrated embodiment, coils 44, 46, 48 are disposed in proximal tip portion 62 of tip assembly 54. In another embodiment the coils may further extend at least partially into the intermediate tip portion to lessen the distance between the coils and the element. In yet another embodiment, the element may also be arranged to extend closer to the coils by actually being partially within the spring. Coils 44, 46, 48 may alternatively be disposed in member 52 provided that coils 44, 46, 48 are prohibited from bending through, for example, placement in lumens formed in member using a rigid polymer. Coils 44, 46, 48 may be coupled to ECU 24 using conventional conductors 78 (see FIG. 3) extending from proximal end 38 of shaft 36. Coils 44, 46, 48 may be equally spaced circumferentially about axis 74 and may extend parallel to one another and to axis 74. Coils 44, 46, 48 may be oriented in the same way. Alternatively, coils 44, 46, 48 may be oriented or wound in opposite directions for a purpose described hereinbelow. Coils 44, 46, 48 may be disposed about their own internal stationary ferrite cores to increase the inductance of coils 44, 46, 48. In one embodiment ferrite 50 is not wrapped with a coil. Although three coils 44, 46, 48 are shown in the illustrated embodiment, it should be understood that the number of coils may vary depending on the degree of precision and the components of force to be determined In particular, and with reference to FIG. 4, a single coil 44, 46 or 48 may be employed and provide a less accurate but possibly adequate measure of minimum net contact force as described above. The use of three coils 44, 46, 48 allows a determination of the deformation of the distal end 40 of catheter 16 in three-dimensional space and, therefore, the provision of a three-dimensional force vector (of distal portion 64 relative to proximal portion 68) representing the contact force magnitude and orientation.

Referring again to FIGS. 2-3, element 50 effects various electrical characteristics of coils 44, 46, 48. In particular, the axial and angular position of element 50 relative to coils 44, 46, 48 and the physical properties of element 50 effect various electrical characteristics of coils 44, 46, 48. Element 50 may be electrically passive in that no net current is input to or output from element 50 as by a wired connection. As a result, no interconnect conductors necessarily extend from element 50 through shaft 36 thereby conserving valuable space within catheter 16. Element 50 may be made, however, from a material that effects an electrical characteristic in each of coils 44, 46, 48. Element 50 may include a magnetically permeable member and, in particular, a member having a magnetic permeability larger than the magnetic permeability of air. Element 50 therefore influences magnetic fields produced by coils 44, 46, 48 in some embodiments. Therefore, if a coil 44, 46, 48 is excited, the degree to which the coil 44, 46, 48 will develop a magnetic field will be influenced by how well that forming magnetic field is coupled into element 50. Movement of element 50 relative to coils 44, 46, 48 reproducibly affects the magnetic field created by each coil 44, 46, 48 if excited in a predetermined manner such as with a current pulse. Therefore, measuring or detecting the magnetic fields of each coil 44, 46, 48 such as by detecting the growth, steady state or decay of those fields or the electrical currents involved in their formation or decay, permits one to determine the position of element 50 and distal tip portion 70 of shaft 36 relative to coils 44, 46, 48. These measurements may be made using various circuits for sensing current, voltage or resonant frequencies.

In accordance with certain embodiments of the present teachings, element 50 may comprise a ferrite. Ferrites concentrate (amplify) magnetic fields and allow larger fields to be created because ferrites have a relatively high magnetic permeability (i.e., they concentrate and intensify magnetic fields). In accordance with other embodiments of the present teachings, element 50 may comprise an unpoled magnetic material. Element 50 is configured for movement with distal portion 70 of shaft 36 (again, in an alternate embodiment, the positions of coils 44, 46, 48 and element 50 may be reversed such that coils 44, 46, 48 are configured for movement with distal portion 70 of shaft 36). Movement of distal portion 70 of shaft 36 and, therefore, movement of element 50 causes a change in an electrical characteristic of each coil 44, 46, 48 that is indicative of a specific deformation of distal portion 70 of shaft 36 and also a specific contact force between the distal portion 70 of shaft 36 and tissue 12. For example, movement of element 50 will cause a change in inductance in each coil 44, 46, 48. In particular, if intermediate tip portion 66 is compressed axially in response to contact of the distal end 40 of shaft 36 with tissue 12, the inductance in each coil 44, 46, 48 will increase as element 50 moves closer to coils 44, 46, 48. If distal tip portion 64 bends relative to axis 74 in response to contact of the distal end 40 of shaft 36 with tissue 12, the inductance in certain coils 44, 46, 48, will increase while the inductance in other coils 44, 46, 48, will decrease as element 50 moves closer to certain coils 44, 46, 48 and farther away from other coils 44, 46, 48 and angulates relative to the coils 44, 46 48. In addition to effecting the electrical characteristic of coils 44, 46, 48 the material of element 50 may be selected to provide radiographic contrast relative to other portions of catheter 16 such that element 50 serves as a fiducial marker during fluoroscopic imaging or may be selected to minimize thermal gradients in catheter 16 during, for example, ablation. Element 50 may be made from materials that are rigid or flexible. Preferred materials are ceramic or metal-ceramic ferrites.

The magnitude of change in the measured electrical characteristic will be affected by several design considerations. These considerations include: (1) the distance between coils 44, 46, 48 and element 50 (the smaller the distance between coils 44, 46, 48 and element 50, the larger the starting inductance in coils 44, 46, 48 will be in the absence of any contact force); (2) the size and/or magnetic permeability of element 50 (elements 50 that are larger in size or have larger magnetic permeability will result in increases in larger coupling in all states of deflection); (3) the inductance of the coils 44, 46, 48 in the absence of element 50; (4) the ratio of the diameter or size of the element 50 to the distance between coils 44, 46, 48 and element 50; (5) the shape of element 50 (e.g., solid or tubular); and (6) the insulative or conductive properties of element 50. Further, the direction of coil-winding of coils 44, 46, 48 will determine the sense (direction) of the magnetic fields. A larger number of coil windings N will also increase inductances.

Figure 5:
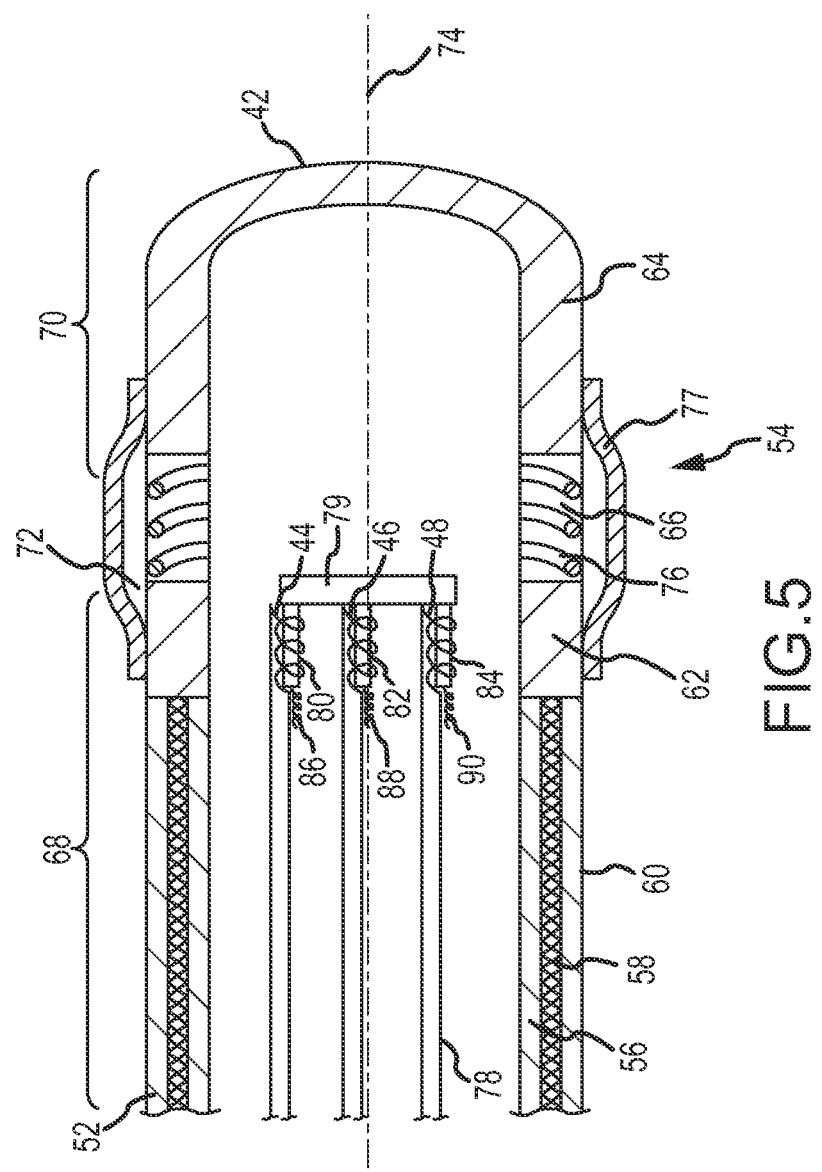
FIG. 5 is a sectional view of a portion of a medical device for diagnosis or treatment of tissue in accordance with another embodiment of the present teachings.

Element 50 may be disposed in distal tip portion 64 of shaft 36 and axially spaced from coils 44, 46, 48 as shown in FIGS. 2-3. Referring to FIG. 5, in an alternative embodiment, an element 79 may include protrusions 80, 82, 84 extending within one or more of coils 44, 46, 48 such that element 79 is at least partially disposed within and surrounded by coils 44, 46, 48. In this embodiment, element 79 engages a proximal end of distal portion 70 of shaft 36 of catheter 16 (e.g. the proximal end of intermediate tip portion 66) As depicted in FIG. 5, element 79 can be rigidly mounted to distal portion 70. Movement of distal portion 70 relative to portion 68 causes any change in overlap of the element 79, protrusions 80, 82, 84, and coils 44, 46, 48. The spring 76 allows relative movement of coils 44, 46, 48 to element 79. Similarly, as depicted in FIG. 4, coil 44 is rigidly mounted to tip 70 and element 50 is rigidly attached to portion 68. Movement of the distal portion 70 of shaft 36 in response to contact force between the distal end 40 of catheter 16 and tissue 12 causes movement of element 50. In yet another embodiment, the medical device includes both element 50 and element 79.

Figure 6:
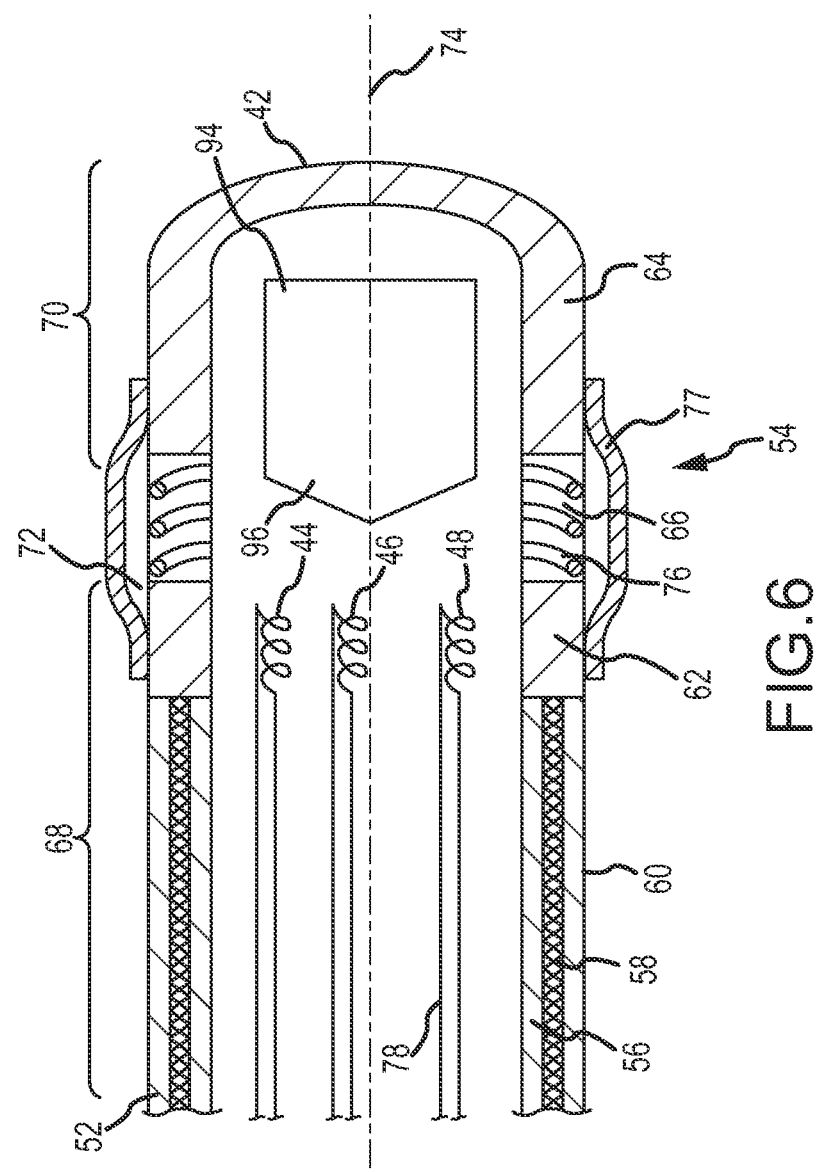
FIG. 6 is a sectional view of a portion of a medical device for diagnosis or treatment of tissue in accordance with another embodiment of the present teachings.
Figure 7:
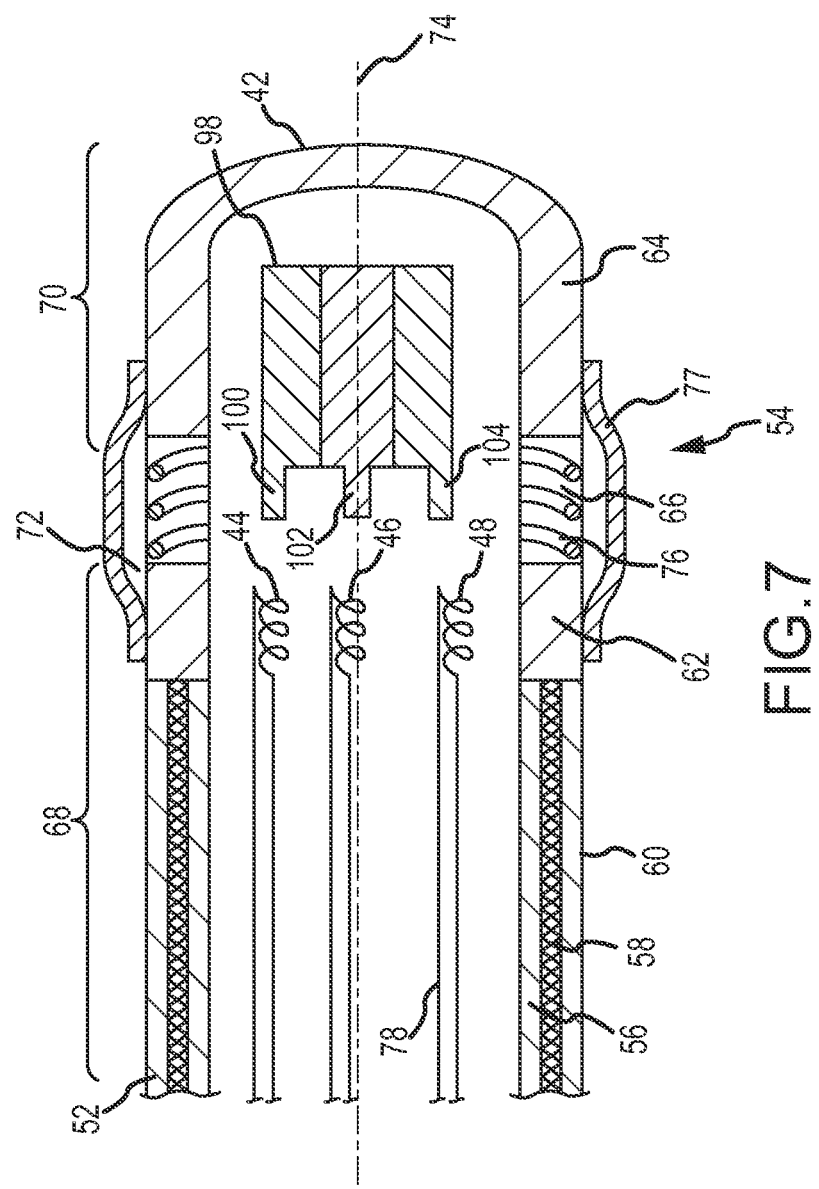
FIG. 7 is a sectional view of a portion of a medical device for diagnosis or treatment of tissue in accordance with another embodiment of the present teachings.

Element 50 (and element 79) may assume a variety of shapes or configurations. Referring again to FIG. 2, in one embodiment, element 50 is cylindrical in shape within a central aperture 92 extending therethrough (i.e., element 50 is annular in cross-section). Aperture 92 may serve as a lumen for passage of irrigation or body fluids or for an RF conductor or a temperature sensor. Element 50 need not be cylindrical, however, and may not include aperture 92. Further, the inner and outer diameters of element 50 may vary. In the illustrated embodiment, element 50 also has an axial end face opposing coils 44, 46, 48 that is flat. Referring to FIG. 6, however, in another embodiment an element 94 may alternatively define a conically shaped proximal end 96 such that a center portion of element 94 extends further axially towards coils 44, 46, 48 than radially outer portions of element 94. In this manner, the center portion of element 94 can be oriented closer to coils 44, 46, 48 than element 94 while still permitting element 94 to move with distal portion 70 of catheter 16 without physically interfering with coils 44, 46, 48. Element 94 may even be arranged such that the pointed conical tip of element 94 is disposed between coils 44, 46, 48 and is radially aligned with at least a portion of coils 44, 46, 48 when a sufficient contact force is applied to distal end 70 of catheter 16 or even in the absence of a contact force on distal end 70 of catheter 16. Again, element 94 is rigidly mounted to section 70 and coils 44,46,48 rigidly attached to portion 68. Referring to FIG. 7, in yet another embodiment, an element 98 may include a plurality of protrusions 100, 102, 104 extending axially from a proximal end of element 98 such that protrusions 100, 102, 104 are nearer to coils 44, 46, 48 than the axial end face of element 98. Each protrusion 100, 102, 104, may be aligned with a corresponding coil 44, 46, 48 and may extend sufficiently far such that one or more of the protrusions 100, 102, 104 are at least partially surrounded by coils 44, 46, 48 when a sufficient contact force is applied to distal end 70 of catheter 16 or even in the absence of a contact force. The distal end of each coil 44, 46, 48 may be wider than the remainder of coils 44, 46, 48 to accommodate protrusions 100, 102, 104. Although elements 50, 79, 94 and 98 are each illustrated as unitary, one-piece bodies, it should be understood that any of elements 50, 79, 94 and 98 could alternatively be formed as a plurality of members or bodies separated by air or a physical-joining material.. Further, although elements 50, 94 and 98 are shown as a separate body, elements 50, 94, and 98 may be formed as an extension of tip electrode 42 (e.g., element 50, 94 or 98 may be partially coated with platinum or another conductor to serve as the electrode 42).

Referring again to FIG. 1, ablation generator 18 generates, delivers and controls ablating radiofrequency energy used by catheter 16. Generator 18 includes a radiofrequency generator 106 configured to generate an ablation signal that is output across a pair of source connectors: a positive polarity connector which may connect to electrode 42 on catheter 16; and a negative polarity connector which may be electrically connected by conductors or lead wires to a patch electrode (not shown) on body 14. It should be understood that the term connectors as used herein does not imply a particular type of physical interface mechanism, but is rather broadly contemplated to represent one or more electrical nodes. Generator 18 is configured to generate a signal at a predetermined frequency in accordance with one or more user specified parameters (e.g., power, time, etc.) and under the control of various feedback sensing and control circuitry as is known in the art. Ablation generator 18 may also monitor or control various parameters associated with the ablation procedure including impedance, the temperature at the tip of catheter 16, ablation energy, irrigant flow rate and the position of the catheter 16 and provide feedback to the physician regarding these parameters.

RCGS 20 may be provided to manipulate catheter 16. In particular, RCGS 20 permits control of translation, distal bending, and virtual rotation of catheter 16 and any surrounding sheath. RCGS 20 therefore provides the user with a type of control similar to that provided by conventional manually-operated systems, but allows for repeatable, precise, and dynamic movements. A physician may identify target locations (potentially forming a path) on an image of tissue 12. RCGS 20 relates these digitally selected points to positions within the patient's actual/physical anatomy, and may thereafter command control the movement of catheter 16 to the defined positions where the physician or the RCGS 20 can perform the desired diagnostic of therapeutic function. A more complete description of various elements of an RCGS may be found in the following patent applications that are incorporated herein by reference in their respective entireties: International Patent Application Publication No. WO 2009/120982 published Oct. 1, 2009; U.S. Patent Application Publication No. 2009/0247942 published Oct. 1, 2009; U.S. Patent Application Publication No. 2009/0247944 published Oct. 1, 2009; U.S. Patent Application Publication No. 2009/0247993 published Oct. 1, 2009; U.S. Patent Application Publication No. 2009/0248042 published Oct. 1, 2009; U.S. Patent Application Publication No. 2010/0256558 published Oct. 7, 2010; and U.S. Patent Application Publication No. 2011/0015569 published Jan. 20, 2011. Although particular embodiments of an RCGS 20 are described and illustrated in the aforementioned applications, it should be understood that RCGS 20 may assume a variety of different embodiments. For example, RCGS 20 may comprise any of the systems offered for sale by Hansen Medical, Inc. under the trademarks "Magellan" and "Sensei." RCGS 20 may also comprise a magnetic navigation system such as the system offered for sale by Stereotaxis, Inc. under the trademark "Epoch" in which magnetic fields are used to guide an ablation catheter having a magnetic member that is responsive to the generation of the magnetic fields.

Display system 22 is provided to convey information to a physician to assist in diagnosis and treatment. Display system 22 may comprise one or more conventional computer monitors or other display devices. Display system 22 presents a graphical user interface (GUI) to the physician. The GUI may include a variety of information including, for example, an image of the geometry of tissue 12, electrophysiology data associated with the tissue 12, graphs illustrating voltage levels over time for various electrodes 42 and images of catheter 16 and other medical devices and related information indicative of the position of catheter 16 and other devices relative to the tissue 12.

ECU 24 provides a means for controlling delivery of ablation energy by ablation catheter 16 to tissue 12 and for controlling the operation of various components of system 10 including catheter 16, ablation generator 18, RCGS 20, and display system 22. ECU 24 may further form part of a system for determining the position and orientation of catheter 16 and similar devices within body 14 such as the system offered for sale under the trademark EnSite™ NavX™ by St. Jude Medical, Inc. and described in U.S. Pat. No. 7,263,397, the entire disclosure of which is incorporated herein by reference or the system such as the MediGuide™ Technology offered for sale by St. Jude Medical, Inc. and generally shown and described in, for example, U.S. Pat. No. 7,386,339, the entire disclosure of which is incorporated herein by reference. ECU 24 may comprise one or more programmable microprocessors or microcontrollers or may comprise one or more ASICs. ECU 24 may include a central processing unit (CPU) and an input/output (I/O) interface through which ECU 24 may receive a plurality of input signals including signals generated by ablation generator 18, electrodes 42 and coils 44, 46, 48 on catheter 16, and RCGS 20 and generate a plurality of output signals including those used to control and/or provide data to electrodes 42 and coils 44, 46, 48 on catheter 16, ablation generator 18, RCGS 20 and display system 22.

In accordance with one aspect of the present teachings, ECU 24 provides a means for determining a contact force between the distal end 40 of catheter 16 and tissue 12. ECU 24 may be configured with programming instructions from a computer program (i.e., software) to implement a method for determining a contact force between the distal end 40 of catheter 16 and tissue 12. The program may be stored in a local memory associated with ECU 24, a remote memory accessible by ECU 24 over a telecommunications network (e.g., on a file server) or on a portable storage medium such as a compact disc or on other types of computer readable storage mediums. ECU 24 determines the contact force responsive to signals generated by coils 44, 46, 48 on catheter 16 that are indicative of a change in an electrical characteristic of each coil 44, 46, 48. As discussed hereinabove, elements 50, 79, 94 and 98, have an effect on an electrical characteristic (e.g., an inductance related characteristic) associated with each coil 44, 46, 48. In the absence of any contact force between the distal end 40 of catheter 16 and tissue 12 (i.e. in an uncompressed and unbent state), the electrical characteristic has one value. Movement of distal portion 70 of shaft 36 and, therefore, movement of elements 50, 79, 94 and 98 typically causes changes in each of the electrical characteristics of coils 44, 46, 48 such that the electrical characteristics assume new values. These changes taken together in the electrical characteristics provide an indication of the contact force between the distal end 40 of catheter 16 and tissue 12 and the position and orientation of the distal end 40 of catheter 16. ECU 24 may be configured to measure changes in a variety of electrical characteristics associated with coils 44, 46, 48 including inductance, the resonant frequency of each coil 44, 46, 48 the inductive or capacitive coupling of each coil 44, 46, 48 or the loss in resistance in each coil 44, 46, 48. As an example, an equal change in an electrical characteristic on all three coils 44, 46, 48 indicates a uniform compression (or stretching) of the distal portion 70 of shaft 36 whereas any unequal changes corresponding to a bending of distal portion 70.

In accordance with one embodiment of the present teachings, ECU 24 does not itself supply current to coils 44, 46, 48 and only measures the change in the electrical characteristic of each coil 44, 46, 48 in response to movement of element 50, 79, 94 or 98. In accordance with other embodiments of the present teachings, ECU 24 itself drives or excites one or more coils 44, 46, 48 and measures the change in the electrical characteristic on the driven and/or undriven coils 44, 46, 48. For example, in one embodiment, ECU 24 may supply current to one coil 44 and detect the change in an electrical characteristic on each of the remaining coils 46, 48 such as the change in inductance on coils 46, 48 resulting from the supply of current to coil 44 as modulated by movement of element 50, 79, 94 or 98. ECU 24 may perform this action for each coil such that ECU 24 supplies current to coil 44 and measures the change in an electrical characteristic on coils 46, 48 then supplies current to coil 46 and measures the change in an electrical characteristic on coils 44, 48 and then supplies current to coil 48 and measures the change in electrical characteristic on coils 44, 46 (and may further repeat this cycle). In another embodiment, ECU 24 may supply current to multiple coils, such as coils 44, 46 and measure a change in an electrical characteristic of the remaining coil 48 (or coils where more than three coils are used). ECU 24 may again perform this action for each coil or coils such that ECU supplies current to coils 44, 46 and measures the change in an electrical characteristic on coil 48, then supplies current to coils 46, 48 and measures the change in an electrical characteristic on coil 44 and then supplies current to coils 44, 48 and measures the change in electrical characteristic on coil 46 (and may further repeat this cycle). In each of these embodiments, ECU 24 may be configured to compare a value of the signal generated by a given coil 44, 46, 48 to a stored value indicative of the electrical characteristic of the coil 44, 46, 48 in the absence of a contact force on the distal end 40 of catheter 16.

In another embodiment, ECU 24 may be configured to compare a value of the signal generated by a given coil 44, 46, 48 to a computed modeled value indicative of the electrical characteristic of the coil 44, 46, 48 in the absence of a contact force on the distal end 40 of catheter 16. The stored values may be stored, for example, in a look up table or other conventional data structure stored in a memory internal or external to ECU 24. In yet another embodiment, ECU 24 may supply current to one or more coils 44, 46, 48 in order to cancel out or negate the value of the electrical characteristic in a particular coil 44, 46, 48 that exists in the absence of a contact force between catheter 16 and tissue 12. As set forth above, an electrical characteristic associated with each coil will have an initial or default value even in the absence of contact force due to the presence of element 50, 79, 94 or 98 and/or other external factors. ECU 24 may supply current to one of coils 44, 46, 48 for the purpose of cancelling or negating this initial or default value. For example, ECU 24 may supply current to one coil, such as coil 44, in such a way as to cancel or negate an initial or default inductance value in the other coils 46, 48 that exists in the absence of contact force. In this manner, ECU 24 calibrates the signal measurements such that the measured value of the electrical characteristic is due solely to movement of element 50, 79, 94 or 98. Coils 44, 46, 48 may be oriented or wound in opposite directions to facilitate this embodiment.

Another general advantage of a 3 coil/single ferrite system versus a single coil/single ferrite system, in addition to superior accuracy and independent sensing of all force magnitudes and orientations, is that any unwanted zero-force deflections in the tip can be accurately canceled out or tared out as these undesired initial "zero" deflection can also be sensed accurately with respect to magnitude and direction.

Field generator 26 may be provided to allow for alternative external wireless excitation of coils 44, 46, 48. Although ECU 24 may be used to drive or excite coils 44, 46, 48 through conductors extending to coils 44, 46, 48 it may alternatively be desired to excite coils 44, 46, 48 using an external field generator (external to at least catheter 16, but potentially body 14 s well). Field generator 26 generates one or more magnetic fields (with a magnitude and direction). In one embodiment, field generator includes a set of three orthogonally arranged coils arranged to create magnetic fields within an area including body 14 and to control the strength, orientation and frequency of the fields. Field generator 26 may comprise a magnetic field generator such as the MediGuide™ Technology offered for sale by St. Jude Medical, Inc. or the generator sold under the trademark "CARTO" by Biosense Webster, Inc. It will be appreciated that if field generator 26 is used to excite coils 44,46,48 that one is exciting both the coils and the ferrite at the same time from all sides. However the coil electrical behavior will still be a unique function of the position/orientation of the ferrite. The coils may also be employed as a part of a three dimensional navigation system as well.

A medical device and system 10 in accordance with the present teachings is advantageous relative to conventional devices and systems. A medical device and system 10 in accordance with the present teachings provide a means for measuring contact force (at least the magnitude of the axial/bending vector subcomponents if not preferably also the spatial orientations of said vector components) between the device and tissue 12 in the body 14 that is less complex and less expensive than conventional devices and systems. For example, in one conventional catheter, a transmitting coil is disposed in a distal tip of the catheter and a plurality of receiving coils are disposed in a proximal portion of the catheter on the other side of a calibrated spring. The position of the transmitting coil relative to the receiving coils, and therefore the force exerted on the distal tip of the catheter across the spring, is determined responsive to signals generated by the receiving coils to provide an indication of contact force. Details regarding this exemplary catheter may be found in U.S. Pat. No. 8,357,152 and U.S. Patent Application Publication No. 2009/0138007 published May 28, 2009, the entire disclosures of which are incorporated herein by reference. This arrangement of transmitting and receiving coils, however, requires multiple conductive leads to each of the coils including two leads which must pass through the spring. Available space within catheters and similar medical devices is limited due to the size and intended use of the devices. Routing conductors to each coil consumes valuable space within the device and increases manufacturing costs. The use of an electrically passive element 50, 79, 94 or 98 in the distal portion 70 of the device reduces the number of conductors 78 needed within the device for determining contact force as compared to conventional devices. As a result, the device and system 10 conserve valuable space within the device and are less expensive to manufacture. Further, any coil wire through the spring which is eliminated also eliminates its potential in altering the apparent stiffness of the spring.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the present disclosure, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for a treatment or diagnosis of tissue within a body, comprising:
    an elongate, tubular shaft configured to be received within the body, said shaft having a proximal portion and a distal portion configured for movement relative to a distal end of the proximal portion including by movement towards and away from the distal end of the proximal portion along a longitudinal axis of said shaft and by deflection from the longitudinal axis;
    a flexible member disposed between the proximal and distal portions of said shaft, said flexible member having a predetermined stiffness;
    a first electromagnetic coil disposed within said proximal portion of said shaft; and,
    a first electrically passive element disposed within said distal portion of said shaft, said first electrically passive element comprising a material effecting an electrical characteristic of said first electromagnetic coil;
    wherein said first electrically passive element is configured for movement with the distal portion of the shaft and relative to said first electromagnetic coil, relative movement between said first electromagnetic coil and said first electrically passive element in response to contact of the distal portion with the tissue and deformation of said flexible member causing a change in the electrical characteristic in said first electromagnetic coil, the change indicative of said deformation of said flexible member and at-least a contact force magnitude between the distal portion and the tissue;
    wherein the proximal and distal portions of said shaft are rigid relative to said flexible member; and
    wherein said first electrically passive element is configured to be at least partially disposed within said first electromagnetic coil.

2. The medical device of claim 1 wherein at least a portion of said first electrically passive element is axially spaced from said first electromagnetic coil.

3. The medical device of claim 1 wherein said electrically passive element comprises one of a flat end face, a conical end face, and a central hole or bore generally facing the first electrically passive element.

4. The medical device of claim 1, wherein said first electrically passive element comprises an element which includes protrusions which project closer or into to an opposed coil.

5. The medical device of claim 1 wherein said first electrically passive element comprises a magnetically permeable member having a magnetic permeability larger than a magnetic permeability of air.

6. The medical device of claim 5 wherein said magnetically permeable member comprises a ferrite.

7. The medical device of claim 1 further comprising second and third electromagnetic coils disposed within said shaft, said first, second and third electromagnetic coils extending parallel to the longitudinal axis and equally spaced from each other circumferentially about the longitudinal axis.

8. The medical device of claim 7 wherein said first electrically passive element comprises one of a rotationally symmetric shape about the longitudinal axis, a torus, annulus, disc or ring shape centered on the longitudinal axis, and an element which includes protrusions which project closer or into to an opposed coil.

9. The medical device of claim 7 wherein the first, second and third electromagnetic coils create one of magnetic fields all of the same rotational direction about a catheter axis and magnetic fields about the catheter axis which are of opposed rotational direction about the catheter axis.

10. The medical device of claim 7 wherein the combination of three coils and one passive element further allows determination of both axial and bending contact force vector magnitudes, as well as determination of both axial and bending contact vector directions.

11. The medical device of claim 10 wherein the coils are rigidly attached to the shaft on a first side of the flexible member and the passive element is rigidly attached to the shaft on the opposite second side of the flexible element.

12. A system for a treatment or diagnosis of tissue within a body, comprising:
a medical device, comprising:
an elongate, tubular shaft configured to be received within the body, said shaft having a proximal portion and a distal portion configured for movement relative to a distal end of the proximal portion including by movement towards and away from the distal end of the proximal portion along a longitudinal axis of said shaft and by deflection from the longitudinal axis;
a flexible member disposed between the proximal and distal portions of said shaft, said flexible member having a predetermined stiffness;
a first electromagnetic coil disposed within said proximal portion of said shaft; and,
a first electrically passive element disposed within said distal portion of said shaft, said first electrically passive element comprising a material effecting an electrical characteristic in said first electromagnetic coil,
wherein said first electrically passive element is configured for movement with the distal portion of the shaft and relative to said first electromagnetic coil, relative movement between said first electromagnetic coil and said first electrically passive element in response to contact of the distal portion with the tissue and deformation of said flexible member causing a change in the electrical characteristic in said first electromagnetic coil, the change indicative of said deformation of said flexible member and a contact force magnitude between the distal portion and the tissue; and,
wherein the proximal and distal portions of said shaft are rigid relative to said flexible member; and
wherein said first electromagnetic coil is configured to be deflectably disposed about a portion of said first electrically passive element; and
an electronic control unit configured to determine a specific contact force magnitude responsive to a signal generated by said first electromagnetic coil indicative of the change in the electrical characteristic of said first electromagnetic coil.

13. The system of claim 12 wherein said electronic control unit is further configured, in determining one or more of a specific contact force magnitude or a specific contact force vector direction by one or both of using a lookup table of coil response data to determine a deflection force magnitude or orientation and using a model to compute what deflection force magnitude and orientation would cause an observed coil response.

14. The system of claim 12, wherein said first electrically passive element comprises an element which includes protrusions which project closer or into to an opposed coil.

15. The system of claim 12 wherein said medical device includes at least one conductor extending from the first electromagnetic coil disposed within said shaft to a proximal end of said medical device and said electronic control unit is further configured, in determining said contact force to generate a current on said at least one conductor and in the first electromagnetic coil, the current exciting the first electromagnetic coil, the first electromagnetic coil excitation or the decay thereof being predictably influenced by the deflection state of the passive element relative to the first electromagnetic coil.

16. The system of claim 15 further comprising a magnetic field generator disposed outside of said medical device and configured to generate a current in said first electromagnetic coil.

17. The system of claim 12 further comprising second and third electromagnetic coils disposed within said shaft, said first, second, and third electromagnetic coils extending parallel to the longitudinal axis and equally angularly spaced from each other circumferentially about the longitudinal axis, wherein the first, second, and third electromagnetic coils are configured to allow for determination of the contact force magnitudes and spatial directions of both the axial and bending contact force component vectors.

18. The system of claim 17 wherein said first electrically passive element comprises a magnetically permeable member having a magnetic permeability larger than a magnetic permeability of air.

19. The system of claim 17 wherein at least a portion of said first electrically passive element is axially spaced from said first electromagnetic coil.

20. The system of claim 17 wherein said flexible member comprises a spring which has a known stiffnesses in both an axial compression direction and a bending direction, wherein the spring contains no wired connection to an electromagnetic coil.

* * * * *